(12) United States Patent  (10) Patent No.: US 8,237,113 B2
Schürenberg  (45) Date of Patent: Aug. 7, 2012

(54) PREPARATION OF A MATRIX LAYER FOR SPECTROMETRY

(75) Inventor: Martin Schürenberg, Tarmstedt (DE)

(73) Assignee: Bruker Daltonik GmbH, Bremen (DE)

( * ) Notice: Subject to any disclaimer, the term of this patent is extended or adjusted under 35 U.S.C. 154(b) by 1232 days.

(21) Appl. No.: 11/955,577

(22) Filed: Dec. 13, 2007

(65) Prior Publication Data

US 2008/0142703 A1   Jun. 19, 2008

(30) Foreign Application Priority Data

Dec. 18, 2006  (DE) .......................... 10 2006 059 695

(51) Int. Cl.
*H01J 49/26*  (2006.01)
(52) U.S. Cl. ........................................ 250/288; 250/282
(58) Field of Classification Search ................... 250/281, 250/282, 283
See application file for complete search history.

(56) References Cited

U.S. PATENT DOCUMENTS

| | | | |
|---|---|---|---|
| 4,793,339 A | 12/1988 | Matsumoto et al. | 128/200.16 |
| 5,382,793 A | 1/1995 | Weinberger et al. | 250/288 |
| 5,770,272 A | 6/1998 | Biemann et al. | 427/421 |
| 5,808,300 A * | 9/1998 | Caprioli | 250/288 |
| 6,414,306 B1 | 7/2002 | Mayer-Posner et al. | 250/288 |
| 6,825,463 B2 | 11/2004 | Karger et al. | 250/288 |
| 6,855,925 B2 | 2/2005 | Ellson et al. | 250/288 |
| 7,095,018 B2 | 8/2006 | Barnes et al. | 250/288 |
| 7,297,501 B2 | 11/2007 | Diamond et al. | 435/7.1 |
| 2004/0126894 A1 | 7/2004 | Nelson et al. | 436/173 |
| 2005/0153344 A1 * | 7/2005 | Diamond et al. | 435/6 |
| 2005/0156056 A1 | 7/2005 | Larson et al. | 239/102.1 |
| 2005/0232317 A1 * | 10/2005 | Dantus et al. | 372/32 |
| 2006/0063145 A1 | 3/2006 | Suckau et al. | 435/4 |
| 2006/0087651 A1 * | 4/2006 | Montaser et al. | 356/338 |
| 2006/0278824 A1 | 12/2006 | Truche et al. | |
| 2007/0141719 A1 | 6/2007 | Bui | |

FOREIGN PATENT DOCUMENTS

| | | |
|---|---|---|
| DE | 19816359 | 10/1999 |
| JP | 10267806 | 10/1998 |
| WO | WO 97/00422 | 1/1997 |
| WO | WO 2004/051734 | 6/2004 |
| WO | WO 2005/101452 | 10/2005 |
| WO | WO 2006/109073 | 10/2006 |

OTHER PUBLICATIONS

Luxembourg et al.: "Effect of Local Matrix Crystal Variations in Matrix-Assisted Ionization Techniques for Mass Spectrometry", Analytical Chemistry, vol. 75, No. 10, May 15, 2003.

* cited by examiner

*Primary Examiner* — David A Vanore
*Assistant Examiner* — Nicole Ippolito
(74) *Attorney, Agent, or Firm* — O'Shea Getz P.C.

(57) ABSTRACT

The invention relates to preparing a matrix layer on a sample support for mass spectrometric analysis. An aspect of the invention includes detecting a light signal that is attenuated, reflected or scattered by the matrix layer, and using the light signal to examine the matrix layer or to regulate the preparation of the matrix layer.

20 Claims, 1 Drawing Sheet

PREPARATION OF A MATRIX LAYER FOR SPECTROMETRY

PRIORITY INFORMATION

This patent application claims priority from German patent application 10 2006 059 695.1 filed Dec. 18, 2006, which is hereby incorporated by reference.

FIELD OF THE INVENTION

The invention relates to a method for the preparation of a matrix layer on a sample support for mass spectrometric analysis, and in particular to detecting a light signal that is attenuated, reflected or scattered by the matrix layer, and using the light signal to examine the matrix layer or to regulate the preparation of the matrix layer.

BACKGROUND OF THE INVENTION

Over the last 10 to 15 years, mass spectrometric analysis has successfully used matrix assisted laser desorption/ionization (MALDI) for the ionization of biological macromolecules, in particular proteins or peptides.

In matrix assisted laser desorption/ionization, analyte molecules are embedded in a matrix layer. The prepared MALDI sample is irradiated with a short laser pulse that is strongly absorbed by the matrix layer. The pulsed irradiation explosively converts the matrix substance from the solid phase to the gas phase, creating a vaporization cloud (desorption). The analyte molecules are generally ionized by protonation or deprotonation in reactions with the molecules or ions of the matrix substance. The analyte ions are predominantly singly charged after they leave the vaporization cloud.

More than a hundred different chemical matrix substances are known for analyte molecules of different classes of chemical substances, such as proteins or nucleic acids. These include sinapic acid, DHB (i.e., 2,5-dihydroxy-benzoic acid), CHCA (i.e., α-cyano-4-hydroxy cinnamic acid) and HPA (i.e., 3-hydroxypicolinic acid). Only about half a dozen matrix substances have become widely used; different matrix substances have been found optimal for different analytical tasks.

Homogeneous biological samples, such as tissue homogenates, lyzed bacteria or biological fluids (e.g., urine, blood serum, lymph, spinal fluid, tears, sputum) are prepared using a variety of methods, such as "dried droplet" preparation or thin layer preparation. Preparation on the sample support is often preceded by chromatographic or electrophoretic fractionation.

In dried droplet preparation, a matrix solution is pipetted onto a sample support together with analyte molecules, and then dried. The matrix substance crystallizes, and the analyte molecules, present at extremely low concentrations, are embedded in the crystals of the matrix layer, or at their grain boundaries as individual molecules, separated from each other. In thin layer preparation, on the other hand, a suitable matrix solution without any analyte molecules is first pipetted onto the sample support, and a thin, microcrystalline matrix layer is created by quickly evaporating the solvent. A solution containing analyte molecules is then applied to the thin, microcrystalline matrix layer and dried; the sample prepared in this way may, optionally, be washed either during or after the drying process. In both dried droplet preparation and thin layer preparation, the matrix layer can, optionally, be recrystallized by the addition of a suitable solvent.

Imaging mass spectroscopy (IMS) is most often used to examine thin tissue sections rather than homogeneous biological samples. A thin tissue section is prepared, for instance, from a frozen tissue sample taken from a human, animal, or plant organ of interest using a cryomicrotome. It is then placed on an electrically conductive sample support, usually consisting of a glass specimen slide with a transparent conductive coating. A matrix solution is applied to the thin tissue section using an appropriate method. After the matrix layer has dried, the sample slide is inserted directly into the mass spectrometer. The raster scan method according U.S. Pat. No. 5,808,300 to Caprioli or stigmatic imaging of the ions of a small region of the sample as disclosed by S. L. Luxembourg et al., Anal. Chem. 2003; 75, 2333-41 may be used for the subsequent mass spectrometric examination. In addition to thin tissue sections, carriers from thin layer chromatography, gel-electrophoretic membranes or blot membranes may also be considered as samples for imaging mass spectrometric analysis. In these samples, the analyte molecules are already located on the sample support prior to preparation of the matrix layer.

A variety of methods for the preparation of matrix layers for imaging mass spectrometric analysis are known from German patent application DE 10 2006 019 530.2. The matrix solution, or a recrystallization solution, can be applied to the sample by pneumatic spraying, vibration nebulizing or by nanospotting of droplets. The application of the matrix solution is not trivial, because (a) lateral smearing of the analyte molecules must be avoided, (b) the analyte molecules must, as far as possible, be extracted from the sample and incorporated into the crystals of the matrix layer, and (c) a favorable ratio of analyte molecules to contaminants must be achieved.

It has been found that when preparing the matrix layer for imaging mass spectrometric analysis, the matrix solution is favorably applied in the course of several cycles. A large number of individual droplets are applied in each cycle, but not so many that the droplets flow together on the surface to form a liquid film. How much matrix solution is applied, how often, what incubation and drying times are selected, and how fast the drying rate is, are all extremely important for the quality of samples prepared for imaging mass spectrometric analysis. Since little equipment for these procedures is available commercially, they are mostly carried out manually, with the result that only very limited reproducibility is possible. But even when automatic machines are used to apply the matrix solution, important parameters such as the rate of gas flow, the temperature during drying, the proportion of solvent in the air, or the temperature of the sample carrier are generally not held constant.

For these reasons, the preparation of a matrix layer for homogeneous samples is often not adequately reproducible.

A quantitative assessment of the quality of prepared samples has in the past been carried out exclusively by a mass spectrometric control measurement of a known reference substance, in which the presence and intensities (signal strengths) of specified ion signals in the measured mass spectrum are used as a quality criterion.

The preparation of the matrix layer comprises the application and drying of solutions, such as a matrix solution or a recrystallization solution. The recrystallization solution partially dissolves a matrix layer that is already present on the sample carrier. After the drying, analyte molecules from the existing matrix layer, or analyte molecules from the recrystallization solution, are embedded in the prepared matrix layer. If the matrix solution is nebulized to create droplets for application, these droplets may dry when they are still above the sample support, causing a fine "snow" of crystals to land on the sample support. The matrix layer is then prepared by applying a recrystallization solution.

SUMMARY OF THE INVENTION

An aspect of the invention includes detecting a light signal that has, at least partially, been attenuated, reflected or scattered by the matrix layer, and using the light signal to examine the matrix layer or to regulate the preparation of the matrix layer. The light signal is favorably compared for the purposes of the quality check with a reference signal or with specified values.

The light signal can be detected during preparation of the matrix layer, or prior to application of the matrix solution or recrystallization solution, or after the matrix layer has been prepared. Detection may be carried out continuously or at specified times.

These and other objects, features and advantages of the present invention will become more apparent in light of the following detailed description of preferred embodiments thereof, as illustrated in the accompanying drawings.

DETAILED DESCRIPTION

Figure 1:
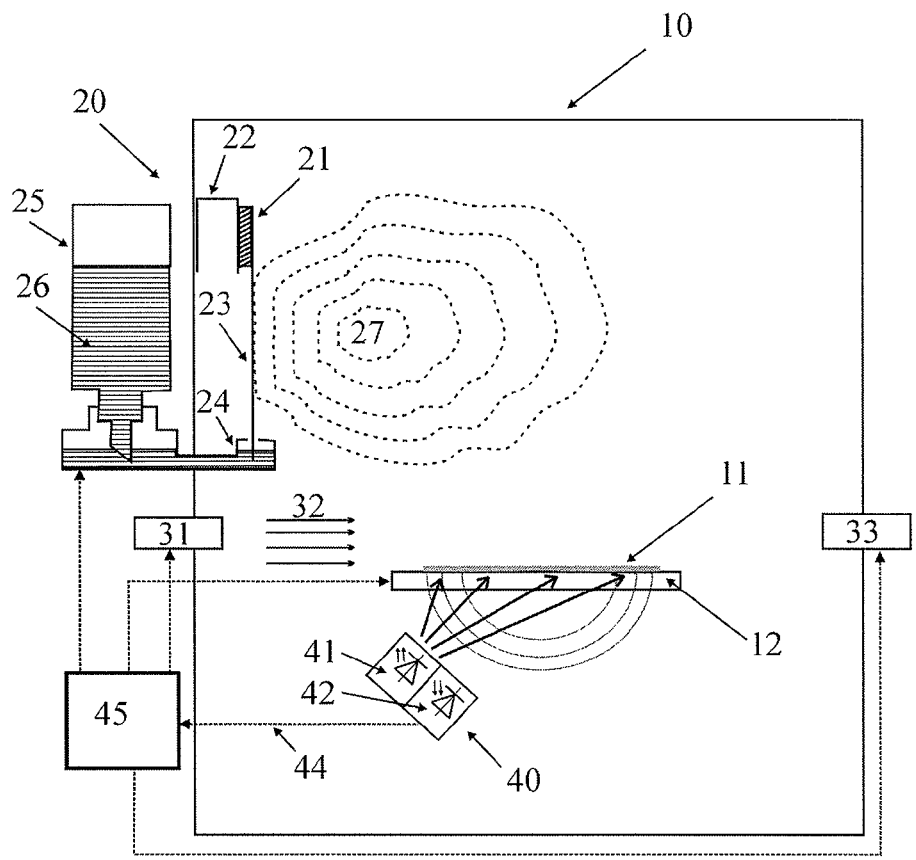
FIG. 1 illustrates a chamber that includes a nebulizing device, a drying device and a sensor for the preparation of a matrix layer on a thin tissue section.

"Matrix layer" also refers here to a matrix layer covered with solutions, or to a matrix layer that is partially dissolved, or a moist matrix layer; the matrix layer may include spatially discrete droplets or by a continuous layer of liquid. The detected light may therefore, according to an aspect of the invention, also be reflected or scattered by the surface of the applied solutions or of the dissolving matrix layer. The light signal may, moreover, be affected by varying degrees of attenuation as the light passes through the matrix layer, depending on the condition of the matrix layer. The attenuation of the light is influenced by the absorption, reflection and scattering effect of the matrix layer.

The matrix solution or the recrystallization solution may be applied in a single cycle or, particularly in the preparation of samples for imaging mass spectrometric analysis, in a large number of cycles.

The quality of the prepared matrix layer is affected, for example, by: the quantity of matrix solution or recrystallization solution applied, the duration of application of the matrix solution or recrystallization solution, the duration of the drying period, the flow rate and temperature of a drying gas that is supplied, the temperature of the sample support, the sequence of the cycles if the matrix solution or the recrystallization solution is applied in a number of cycles.

To date, the practice has merely been to hold as many parameters as possible constant. The method according to an aspect of the invention permits the parameters to be regulated, as an electronically detected light signal provides a quantitative controlled measure. The regulation makes it possible to achieve a matrix layer of a quality that has scarcely been achieved until now and that, moreover, remains constant. It is of special relevance to the preparation of matrix layers for MALDI, and is particularly favorable for imaging mass spectrometric analysis (MALDI imaging). A particular advantage of the method according to an aspect of the invention is that the state of the matrix layer can be monitored in real time during the preparation process.

The quality of the matrix layer can be checked, without carrying out a mass spectrometric analysis in which part of the prepared matrix layer is applied. In addition, the effect of the parameters on the quality of the matrix layer can be determined, permitting targeted optimization of the preparation process. It is also possible to determine specific properties of the matrix layer. Changes to the thickness or density of the matrix layer can be determined by examining the light signal prior to application of the matrix solution and after drying. Furthermore, it is possible to determine quantitatively the proportion of solvent contained in the matrix layer, in other words the degree of drying.

The optical properties of the matrix layer change during preparation. The application of the solution and the subsequent drying both affect absorption, but they particularly affect the scattering and (multiple) reflection by the matrix layer. The reason for this is that a dry matrix layer contains a large number of crystals where light is scattered or undergoes multiple reflections. The application of a solution encloses the crystals in a liquid, causing the refractive index at the boundary surfaces of the crystals to be lowered, so reducing the degree of scattering and reflection. This is, of course, particularly true if the crystals are dissolved by the solution. It is therefore preferable to detect the light that is scattered by the matrix layer, or diffusely reflected by multiple reflections, as this light signal is ideal for distinguishing the different matrix states (partially dissolved, moist, dry). Light that is diffusely reflected as a result of multiple reflections will also be referred to below as scattered light.

It is preferable to use a sensor that incorporates its own light source and a light detector. The electrical light signal from the light detector, optionally electronically amplified and further processed, permits quantitative determination of the state of the matrix layer. The sensor's light source preferably emits infrared light, but it is also possible to use a light source operating in the visible or other part of the spectrum.

The sensor's light source may illuminate the sample support coherently or incoherently. A low-cost light-emitting diode that incoherently illuminates the sample support is preferably used as the light source. It is particularly favorable to use what is known as a reflex sensor, in which the LED and the light detector are housed together in a small, compact sensor, and with which the light scattered back from the matrix layer is detected. If the sample support is transparent to the light emitted by the light source, the reflex sensor may be mounted above or below the sample support; otherwise it may only be fitted above. The light source may, however, also be separate from the light detector. If the attenuation of the light in the matrix layer is measured, the light source and the light detector are located on different sides of the sample support; the sample support must here be transparent to the light emitted by the light source.

In addition to incoherent illumination by a LED, it is also possible for the matrix layer to be coherently illuminated, for example by a laser diode. As the specialist knows, coherent illumination of a rough, scattering surface gives rise to a "speckle pattern". This pattern depends on the state of the matrix layer, and is therefore also suitable as a light signal.

In order to reduce the effect of other light sources in the laboratory, the sensor's light source can be modulated. The light measured in the light detector is subjected to high/low-pass filtering or phase-sensitive amplification, as a result of which the unmodulated background light is largely or entirely suppressed.

The sample support may be illuminated as a whole, or only partially. Partial illumination makes it possible to obtain signals from single, homogeneous samples, from selected tissue regions, or from regions that are free of tissue. The light signals from matrix layers with and without analyte molecules can be compared, to examine the effect of the sample on the preparation. When preparing matrix layers on a thin tissue section it is thus, for instance, possible to determine whether the nature of the sample actually permits the preparation with adequate quality.

In addition to the detected light signal, which is affected by absorption, reflection or scattering of light at the matrix layer, it is possible to detect a reference light signal that preferably does not interact with the matrix layer. The reference light signal makes it possible, for instance, to compensate for changes in a light source over time. If the attenuation of the light as it passes through the matrix layer is used to regulate the preparation of the matrix layer or check its quality, it is preferable for the light signal to be normalized with the aid of the reference light signal.

The features mentioned above, and which will be explained further, may, in accordance with an aspect of the invention, each be exploited singly or in any combination. The embodiments described are not to be understood as a final list, but rather as examples.

FIG. 1 provides a schematic illustration of a preferred arrangement for executing a method in accordance with an aspect of the invention. Prior to the application of a matrix solution, a thin tissue section 11 is first prepared from a frozen sample of tissue using a microtome. As it thaws at room temperature, the frozen thin tissue section 11 immediately spreads out flat on a sample support 12, and adheres to it. Even when dry, the thin tissue sample 11 adheres tightly to the sample support 12. The sample support 12 may be a transparent specimen slide, as used in optical microscopy, to whose surface a transparent but electrically conductive coating has been applied for the purposes of later use in a mass spectrometer.

The thin tissue section 11 on the sample support 12 is placed in a chamber 10 where a nebulizing device 20 is located. The nebulizing device 20 may include for example a nebulizer as disclosed in German Patent Application DE 10 2006 019 530.2. The nebulizer 20 includes a piezoelectric crystal 21 fastened to the chamber 10 by a mount 22 and made to oscillate by the application of a high-frequency alternating voltage. A metal foil 23 is fastened to the piezoelectric crystal 21, with its lower end immersed in a bath 24 containing a matrix solution 26. The matrix solution 26 in the bath 24 is kept at a constant level by a reservoir bottle 25, in the same way as a water dispenser for birds. As soon as the metal foil 23 is made to oscillate by the piezoelectric crystal 21, the matrix solution creeps up the metal foil 23 from the bath 24, and is shaken off in the form of small mist droplets at the antinodes of the oscillation. The result is a cloud of mist 27 that falls onto the thin tissue section 11, causing droplets of the matrix solution 26 to wet the thin tissue section 11. The density with which droplets are applied to the thin tissue section 11 can be adjusted by changing the duration of nebulization, the number of nebulization pulses, and the amplitude of the high-frequency alternating voltage.

After an initial application of the matrix solution 26, the matrix droplets on the thin tissue section 11 are dried by a drying gas 32. The drying gas 32 is supplied through a chamber inlet 31 and withdrawn from a chamber outlet 33. The drying time is determined by the quantity, temperature and duration of the supplied drying gas 32, and also by the proportion of solvent in the air in the chamber 10 and the temperature of the sample support 12.

If the cycle of nebulization of the matrix solution, deposition and drying of the droplets is repeated around ten to twenty times, the thin tissue section 11 can be fully covered with a matrix layer.

In German Patent Application DE 10 2006 019 530.2 the application and drying is carried out without regulation, with the consequence that the quality of the resulting matrix layer varies significantly. This is due to parameters that can only be held constant with great difficulty, if at all. The formation of crystals on the metal foil 23, for instance, affects the nebulization process. The concentration of the matrix solution 26 in the reservoir can also change, as the solvents in the matrix solution 26 are volatile. This also has the effect of raising the proportion of solvent in the air in the chamber 10, thereby influencing the drying of the matrix layer.

A light sensor 40 provides an electrical light signal on a line 44 to a control device 45 that regulates the application and drying of the matrix solution 26. The light signal on the line 44 provides information about the state of the matrix layer, for instance indicating whether the thin tissue section 11 is adequately covered with matrix droplets, or whether the matrix layer has dried sufficiently for the next nebulization cycle to begin. The control device 45 regulates the nebulizing device 20 and the parameters of the drying gas 32. The sample support 12 can also be influenced, for instance, by temperature control.

In this preferred embodiment, the sensor 40 may be a reflex sensor that includes a relatively low-cost LED 41, emitting in the infrared region of the spectrum, and a photodiode 42. The LED 41 illuminates the transparent sample support 12 incoherently from beneath. Light 43 that is scattered back is detected by the photodiode 42. The LED 41 and the photodiode 42 may be housed together, making the sensor 40 very compact. The light from the LED 41 is temporally modulated. The amplified signal from the photodiode is subjected to high/low-pass filtering, as a result of which the signal on the line 44 is not affected, or only very slightly, by ambient background light from the laboratory.

Detecting the light that is scattered back prevents the photodiode 42 from being overdriven by reflections at the matrix layer when the matrix layer is covered with a solution or by a large number of droplets.

If non-transparent sample supports are used, for example made of metal or electrically conductive plastic, it is also possible for the sensor 40 to be positioned above the sample support 12.

Figure 2:
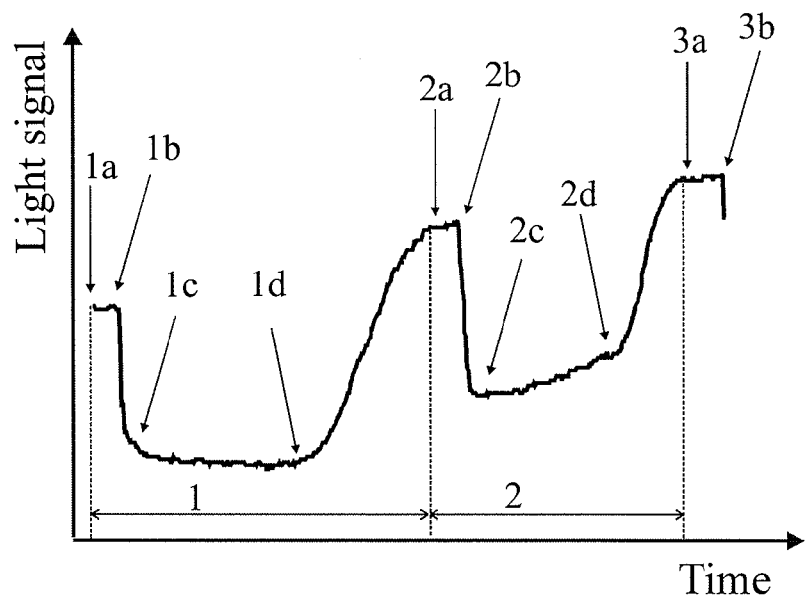
FIG. 2 illustrates the light signal detected from two successive cycles in which a matrix solution is applied to the thin tissue section.

FIG. 2 illustrates a plot of the light signal on the line 44 over a period of two complete cycles. The light signal on the line 44 is constant when the first cycle begins at time 1a. The matrix layer is dry. At time 1b the nebulizing device 20 is switched on via the control device 45, generating the mist cloud 27. As the matrix droplets fall onto the thin tissue section 11, matrix crystals are covered with matrix solution or even begin to dissolve, causing the matrix layer to scatter less light back to the photodiode 42. As can be seen from FIG. 2, the light signal on the line 44 decreases accordingly. The nebulizing device 20 either remains switched on, or is repeatedly switched on briefly by the control device 45, until the light signal on the line 44 decreases to a specified value. Then, starting at time 1c, slow drying begins, without the supply of drying gas 32. The drying is slow because the matrix droplets close to the surface of the thin tissue section 11 generate an atmosphere that is saturated with solvent, as a result of which the drying, in the absence of convection, is diffusion-limited. After a specified period of time, during which analyte molecules are extracted from the thin tissue section 11, the supply of drying gas 32 begins at time 1d. The light signal rises rapidly because the matrix layer now undergoes forced drying, and the light from the LED 41 is again increasingly scattered back at the matrix crystals. At time 2a the light signal on the line 44 reaches saturation, indicating that the matrix layer has again fully crystallized and dried. When the light signal obtained while drying with the drying gas 32 remains constant, the control device 45 initiates further nebulization of the matrix solution 26 at time 2b.

The light signal at time 2a is stronger than the light signal 44 at time 1a. Due to the application of matrix solution in the first cycle, the number of matrix crystals on the thin tissue section 11 has increased, and therefore the intensity of the light that is scattered back to the sensor 40 also increases. The difference between the two light signals can, with the aid of calibration, yield quantitative information about the change in the thickness or density of the matrix layer. The change in the light signal on the line 44 from one cycle to the next is used to regulate the number of cycles. In other words, the control device 45 continues to initiate additional cycles until the light signal 44 from the dry matrix layer has increased by a specified value or has reached a specified value.

As in the first cycle, so again the matrix droplets applied in the second cycle are dried without the supply of the drying gas 32 until time 2c. At time 2d the drying gas 32 is supplied until the matrix layer is completely dry. When repeating cycles it can be advantageous if the matrix layer is not completely dried before nebulization starts again. Complete drying is only carried out to check the thickness of the matrix layer after a specified number of cycles.

Relatively simple and inexpensive equipment can be used to regulate the preparation of a matrix layer or to check its quality without carrying out a mass spectrometric measurement. It has been found that in spite of existing automation, regulating the process by a light signal is crucial for the quality of the prepared matrix layer, particularly, although not exclusively, when preparing samples for imaging mass spectrometric analysis.

Although the present invention has been illustrated and described with respect to several preferred embodiments thereof, various changes, omissions and additions to the form and detail thereof, may be made therein, without departing from the spirit and scope of the invention.

What is claimed is:

1. A method for preparation of a matrix layer for mass spectrometric analysis on a sample support using matrix assisted laser desorption/ionization, comprising detecting a light signal which has been at least partially attenuated by passing through the matrix layer, has been reflected by the matrix layer or has been scattered by the matrix layer, and the light signal is used to regulate the preparation of the matrix layer.

2. The method of claim 1, wherein for the preparation of the matrix layer, a matrix solution, or a recrystallization solution, or dried matrix droplets in the form of a crystal "snow" are applied to the sample support.

3. The method of claim 2, wherein the light signal is detected prior to, during, or after application of the matrix solution or recrystallization solution.

4. The method of claim 2, wherein the matrix solution or recrystallization solution is applied in more than one cycle.

5. The method of claim 4, wherein the light signal is used to regulate one of
the quantity of matrix solution or recrystallization solution applied,
the duration of application of the matrix solution or recrystallization solution,
the duration of the drying period,
the flow rate or temperature of a drying gas that is supplied,
the temperature of the sample support, and
the time sequence of the cycles.

6. The method of claim 4, wherein, from the light signal of two cycles, the quantity of matrix applied or the change in the thickness of the matrix layer is determined.

7. The method of claim 2, wherein the matrix solution is applied by pipetting, by pneumatic spraying, by vibration nebulizing or by nanospotting of droplets.

8. The method of claim 1, wherein analyte molecules are applied to the sample support together with the matrix solution or recrystallization solution.

9. The method of claim 1, wherein analyte molecules are located on the sample support.

10. The method of claim 9, wherein the analyte molecules are located in a thin tissue section.

11. The method of claim 1, wherein the light signal is detected with spatial resolution, or is integrated over the entire sample carrier or over part of the surface of the sample carrier.

12. The method of claim 1, wherein the light from a light source is temporally modulated and the detected light signal is subjected to high pass filtering or to phase-selective amplification in order to minimize the effect of background illumination.

13. The method of claim 1, wherein a reference light signal is additionally detected and the light signal and the reference light signal are used to examine the quality of the matrix layer or to regulate the preparation of the matrix layer.

14. A method for preparing a matrix layer on a sample support for a mass spectrometric analysis using matrix assisted laser desorption/ionization, comprising:
providing a command signal that controls a nebulizer which releases a mist of matrix solution droplets into a chamber;
a sample support onto which a tissue section is placed such that droplets of the matrix solution contact the tissue section;
a light source that emits a beam of light that passes through the sample support and back scatters off the tissue section;
a light detector that senses back scattered light and provides a detected light signal indicative thereof; and
a controller that receives the detected light signal and provides the command signal.

15. The method of claim 14, where the controller controls the flow of a drying gas that dries the tissue section after analyte molecules have been extracted from the tissue section.

16. A system for preparing a matrix layer for mass spectrometry using matrix assisted laser desorption/ionization, comprising:
a nebulizer that receives a command signal and provides a mist of matrix solution droplets to a chamber;
a sample support that supports a tissue section such that the nebulized matrix solution falls onto the tissue section;
a light source that is located below the sample support and emits light which passes the sample Support and strikes the tissue section;
a light detector that is located below the sample support and detects light back scattered off the tissue section and provides a detected light signal indicative thereof;

a controller that receives the detected light signal and provides the command signal based upon the value of the detected light signal.

17. The system of claim 16, where the light detector comprises a photodiode.

18. The system of claim 16, where the light source comprises a light emitting diode.

19. The system of claim 18, wherein the light emitting diode emits infrared light.

20. The system of claim 16, wherein the controller provides a dryer command signal to a means for providing a drying gas to the tissue.

* * * * *